(12) United States Patent
Jiang et al.

(10) Patent No.: US 12,318,557 B2
(45) Date of Patent: Jun. 3, 2025

(54) CATHETER SYSTEM TO PROVIDE NEEDLE SAFETY AND RELATED METHODS

(71) Applicant: Becton, Dickinson and Company, Franklin Lakes, NJ (US)

(72) Inventors: Tao Jiang, Shanghai (CN); Ben Chao, Chiayi (TW)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1035 days.

(21) Appl. No.: 17/339,461

(22) Filed: Jun. 4, 2021

(65) Prior Publication Data

US 2021/0386974 A1  Dec. 16, 2021

Related U.S. Application Data

(60) Provisional application No. 63/039,823, filed on Jun. 16, 2020.

(51) Int. Cl.
*A61M 25/06* (2006.01)
*A61M 39/10* (2006.01)

(52) U.S. Cl.
CPC .... *A61M 25/0618* (2013.01); *A61M 25/0606* (2013.01); *A61M 39/10* (2013.01); *A61M 2039/1077* (2013.01)

(58) Field of Classification Search
CPC .......... A61M 25/0618; A61M 25/0606; A61M 39/10; A61M 2039/1077
USPC ..................................................... 604/164.08
See application file for complete search history.

(56) References Cited

U.S. PATENT DOCUMENTS

| 5,312,371 A | * | 5/1994 | Dombrowski .... | A61M 25/0631 604/263 |
|---|---|---|---|---|
| 5,683,365 A | * | 11/1997 | Brown .............. | A61M 25/0618 604/110 |
| 5,685,860 A | * | 11/1997 | Chang .............. | A61M 25/0618 604/192 |
| 5,957,887 A | | 9/1999 | Oesterlind et al. | |

(Continued)

FOREIGN PATENT DOCUMENTS

BR   112017014390 A2   1/2018
CN   101112639          7/2012

(Continued)

*Primary Examiner* — Phillip A Gray
(74) *Attorney, Agent, or Firm* — Kirton McConkie; Whitney Blair; Kevin Stinger (57) ABSTRACT

A catheter system to protect against needle stick injuries and environmental contamination from exposure to residual blood. The catheter system may include a catheter assembly, a needle assembly, and a housing. The needle assembly may be coupled to the catheter assembly and include a needle hub and an introducer needle. The housing may be secured within a lumen of the catheter adapter and may include a distal end, a proximal end, and a cavity. The introducer needle may extend through the housing. A safety clip within the cavity may include an elongated arm portion and a barrier feature. The introducer needle may bias the barrier feature outwardly away from a longitudinal axis of the introducer needle. In response to proximal retraction of the introducer needle, the barrier feature may be configured to move toward the longitudinal axis of the needle and shield the sharp distal tip.

10 Claims, 9 Drawing Sheets

(56) References Cited

U.S. PATENT DOCUMENTS

| | | | |
|---|---|---|---|
| 7,935,080 B2 * | 5/2011 | Howell | A61M 5/3273 |
| | | | 604/110 |
| 2005/0075609 A1 | 4/2005 | Latona | |
| 2007/0270753 A1 | 11/2007 | Kulli | |
| 2016/0354580 A1 | 12/2016 | Teoh et al. | |
| 2018/0289932 A1 | 10/2018 | Isaacson et al. | |

FOREIGN PATENT DOCUMENTS

| | | |
|---|---|---|
| CN | 205181909 | 4/2016 |
| EP | 1232766 | 8/2002 |
| WO | 2004093961 A1 | 11/2004 |
| WO | 2013/021350 | 2/2013 |

* cited by examiner

CATHETER SYSTEM TO PROVIDE NEEDLE SAFETY AND RELATED METHODS

RELATED APPLICATIONS

This application claims benefit of U.S. Provisional Patent Application No. 63/039,823, filed on Jun. 16, 2020, entitled CATHETER SYSTEM TO PROVIDE NEEDLE SAFETY AND RELATED METHODS, which is incorporated herein in its entirety.

BACKGROUND

Intravenous catheters are traditionally used to infuse fluids, such as saline solution, various medicaments, and/or total parenteral nutrition into a patient. Such catheters may also be used to withdraw blood from a patient, and/or monitor various parameters of the patient's vascular system.

To introduce an intravenous catheter into a patient, an over-the-needle peripheral intravenous ("IV") catheter may be mounted over a hollow-bore introducer needle, which may include a sharp distal tip. The inner surface of the catheter may tightly engage the outer surface of the needle to prevent catheter peel back and facilitate insertion of the catheter into a blood vessel. The tip of the introducer needle may extend beyond the distal tip of the catheter to enable insertion of the catheter at a shallow angle through the patient's skin and into the blood vessel.

To verify proper placement of the needle and the catheter in the blood vessel, the clinician may confirm the presence of "flashback" blood in a flashback chamber associated with the catheter and needle assembly. Once proper placement is confirmed, the clinician may then apply pressure to the blood vessel to occlude the vessel, thereby reducing further blood flow through the introducer needle and catheter. The clinician may then withdraw the needle from the catheter to enable continued access to the blood vessel through the catheter. This process of physically manipulating and disassembling the needle and catheter after the catheter has been properly positioned creates substantial risks of accidental needle sticks and exposure to blood and blood-borne pathogens.

Additionally, it has been observed that withdrawing the needle from a catheter assembly may impart energy to parts of the needle. For instance, during withdrawal of the introducer needle, bending forces can be applied (either unintentionally or intentionally) to the needle. The bending forces on the needle may cause blood to splatter or spray from the needle when the needle vibrates and shakes as it becomes free from the catheter assembly and releases stored energy.

Many serious and contagious diseases, such as Ebola and AIDS, may be transmitted by direct contact with the blood of an infected person. Other serious and contagious diseases, such as SARS, MERS, and COVID-19, are airborne diseases that may be transmitted simply by breathing in or touching a surface that harbors airborne pathogenic organisms, and then touching your own eyes, nose or mouth. In either case, withdrawal of a used needle increases a risk of environmental contamination from exposure to residual blood.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a catheter system to shield a needle after use, and related systems and methods. Embodiments of a catheter system as disclosed herein may protect against needle stick injuries and prevent environmental contamination from exposure to residual blood. In some embodiments, the catheter system may include a catheter assembly, a needle assembly, and a housing. In some embodiments, the catheter assembly may include a catheter adapter and a catheter extending distally from the catheter adapter. In some embodiments, the needle assembly may be coupled to the catheter assembly. The needle assembly may include a needle hub and an introducer needle. In some embodiments, the needle hub may be coupled to a proximal end of the catheter adapter and a proximal end of the introducer needle may be secured within the needle hub.

In some embodiments, the housing may be secured within a lumen of the catheter adapter. The housing may include a distal end and a proximal end, where the proximal end is configured to receive a sharp distal tip of the introducer needle therethrough during assembly. In some embodiments, the housing may further include a cavity, through which a longitudinal shaft of the introducer needle may extend.

In some embodiments, the housing may also include a safety clip located within the cavity. In some embodiments, the safety clip may include an elongated arm portion and a barrier feature. In some embodiments, the introducer needle may bias the barrier feature outwardly away from a longitudinal axis of the introducer needle. In some embodiments, in response to proximal retraction of the introducer needle, the barrier feature may be configured to move toward the longitudinal axis of the needle and shield the sharp distal tip.

In some embodiments, the housing may include a resilient material and/or may be sealed such that blood is contained within the housing. In some embodiments, an outside surface of the housing may include one or more retainer features configured to engage one or more corresponding securement features disposed within the lumen. In some embodiments, the distal end of the housing may be configured to contact or couple to a septum disposed within the lumen to prevent environmental contamination from exposure of residual blood to air.

In some embodiments, the cavity of the housing may include a reinforcement rib to exert a downward force on the safety clip. The downward force may urge the barrier feature against the longitudinal shaft of the introducer needle. In some embodiments, the cavity may include a length sufficient to contain the sharp distal tip and a notch of the introducer needle. In some embodiments, the cavity may include a cutout feature to reduce friction between the cavity and the introducer needle.

In some embodiments, the safety clip may be rigid and/or resilient. In some embodiments, the sharp distal tip of the introducer needle may penetrate the proximal end and/or distal end of the housing such that the longitudinal shaft of the introducer needle may extend through the cavity. In further detail, in some embodiments, the sharp distal tip of the introducer needle may be configured to punch through or form a hole through at least one of the proximal end and the distal end of the housing such that the longitudinal shaft may extend through the cavity.

In some embodiments, a catheter system to shield the needle after use may include a catheter assembly, a needle assembly, and the housing. In some embodiments, the catheter assembly may include the catheter adapter and the catheter extending distally from the catheter adapter. In some embodiments, the needle assembly may be coupled to the catheter assembly and may include the needle hub and the introducer needle. In some embodiments, the needle hub may be coupled to the proximal end of the catheter adapter. In some embodiments, the proximal end of the introducer needle may be secured within the needle hub.

In some embodiments, the housing may be retained within the lumen of the catheter adapter. In some embodiments, the housing may include a first resilient element, a second resilient element proximal to the first resilient element. In some embodiments, the first resilient element may include a coupling element, and the second resilient element may include another coupling element. In some embodiments, the first resilient element and the second resilient elements may each include a proximal end and a distal end. The first resilient element may include a first central bore and the second resilient element may include a second central bore. In some embodiments, the coupling element and the other coupling element may couple the proximal end of the first resilient element to the distal end of the second resilient element such that the first central bore and the second central bore form a central passageway. In some embodiments, the first and second resilient elements may form a V-shape in response proximal retraction of the introducer needle proximal to a distal wall of the first resilient element. In some embodiments, the central passageway may be configured to receive the longitudinal shaft of the introducer needle therethrough.

In some embodiments, the housing may further include a first exterior covering coupled to an outer surface of the first resilient element and/or a second exterior covering coupled to an outer surface of the second resilient element. In some embodiments, the first exterior covering and/or the second exterior covering may each include an aperture to receive the introducer needle therethrough. In some embodiments, the distal end of the first resilient element may be configured to couple to or contact the septum disposed within the lumen.

In some embodiments, in response to the introducer needle extending through the central passageway into the septum, the V-shape may straighten along the longitudinal shaft. In some embodiments, in response to withdrawing the introducer needle proximal to a distal wall of the first resilient element, the V-shape may form such that the sharp distal tip of the introducer needle is secured within the central passageway. In some embodiments, the V-shape may further secure the notch of the introducer needle within the central passageway.

In some embodiments, the first central bore of the first resilient element and/or the second central bore of the second resilient element may be formed by the introducer needle, such as through punching or pushing the introducer needle through the first resilient element and/or the second resilient element. In other embodiments, the first central bore and/or the second central bore may be pre-formed. In some embodiments, the coupling element and/or the other coupling element may each include a protrusion and an aperture disposed at an end.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of some embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

As used in the present disclosure, the term "distal" refers to a portion of a catheter system or component thereof that is farther from a user, and the term "proximal" refers to a portion of a catheter system or component thereof that is closer to the user. Thus, for example, the end of a catheter first touching the body of the patient is a distal end of the catheter, while an opposite end of the catheter is a proximal end of the catheter. As used in the present disclosure, the term "user" may refer to a clinician, doctor, nurse, or any other care provider and may include support personnel.

Figure 1:
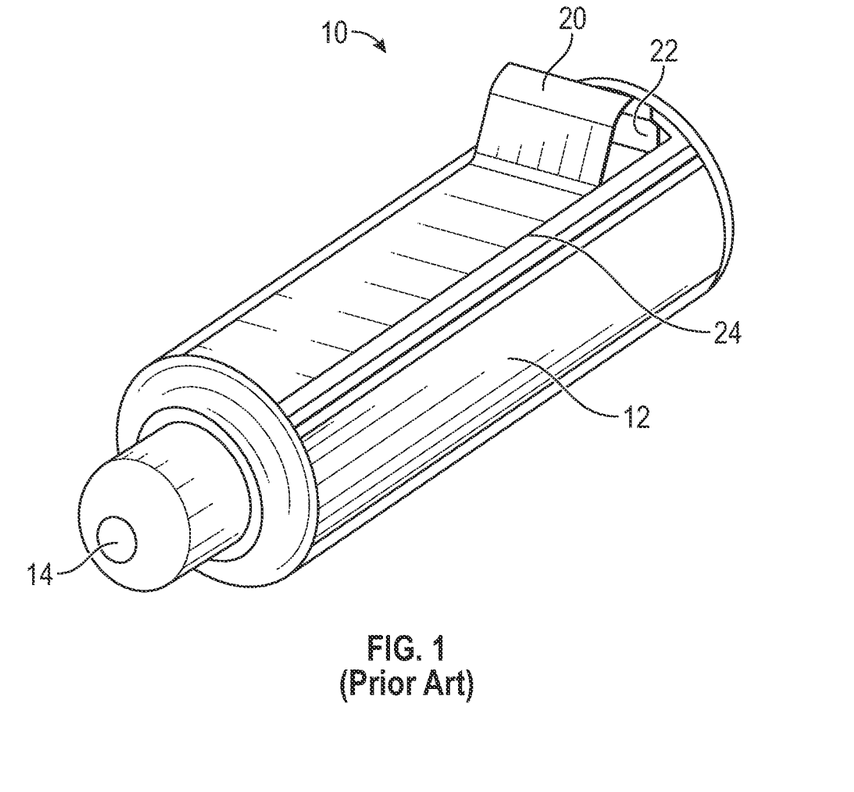
FIG. 1 is a perspective view of a prior art needle safety device for shielding a needle tip.

FIG. 1 illustrates a prior art needle safety device 10 used in the medical field. Typically, the prior art needle safety device 10 is retained within a catheter adapter. The needle extends longitudinally through a body 12 of the prior art needle safety device 10 and a distal opening 14 when the needle is in an insertion position for insertion into vasculature of a patient. After the needle and the catheter are inserted into the vasculature, the needle is retracted proximally to actuate a spring clip 20, which physically shields a sharp distal tip of the needle to prevent a needle stick injury.

The prior art needle safety device 10 may pose several hazards. For example, the prior art needle safety device 10 includes clearance gaps 24 and/or other openings 22 that may expose residual blood on or in the needle directly to the air. When the needle is used to introduce the catheter into the vasculature of the patient, flashback blood may be drawn into the needle. Some blood may remain in the needle after the needle is removed from the catheter. In the process of removing the needle from the catheter, residual blood may fall from the needle and potentially contaminate exposed surfaces and/or the air. Indeed, exposure to residual blood may transmit airborne pathogens of the patient to the user and/or surfaces in a surrounding environment.

The prior art needle safety device 10 is constructed of metal and/or includes one or more sharp edges. This may increase a risk that the patient or a clinician may be cut or scratched, particularly when the prior art needle safety device 10 is removed from the catheter adapter.

Figure 2:
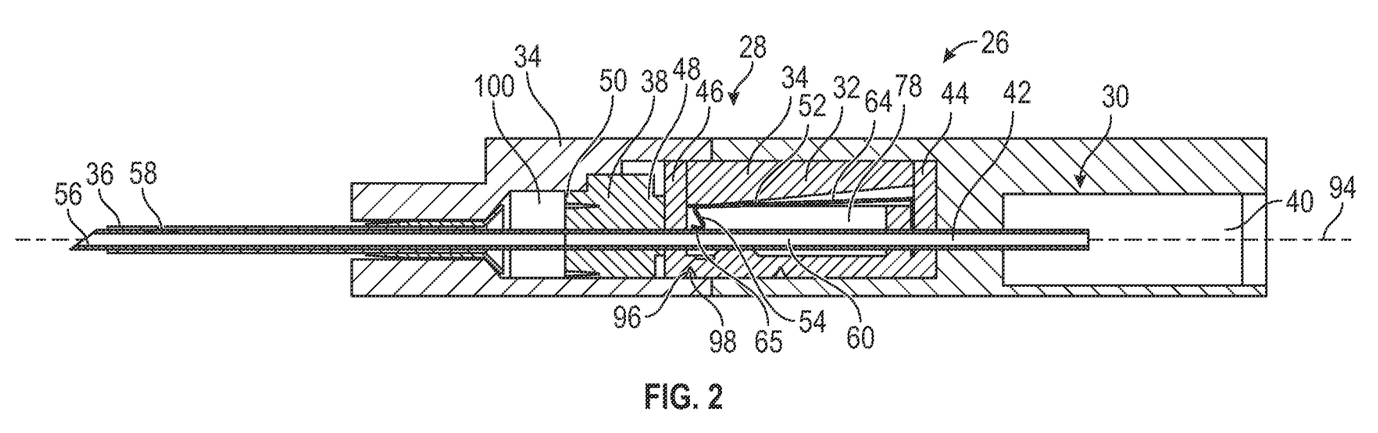
FIG. 2 is a cross-sectional view of an example catheter system to shield an introducer needle after use, illustrating an example introducer needle in an advanced or insertion position, ready for insertion into a patient, according to some embodiments.

Referring now to FIG. 2, a catheter system 26 in accordance with some embodiments may protect against needle stick injuries and prevent environmental contamination from exposure to residual blood. The catheter system 26 may also overcome disadvantages of the prior art, as explained in further detail below. In some embodiments, the catheter system 26 may include a catheter assembly 28, a needle assembly 30, and a housing 32.

In some embodiments, the catheter assembly 28 may include a catheter adapter 34 and a catheter 36 extending from a distal end of the catheter adapter 34. In some embodiments, the needle assembly 30 may be coupled to the catheter adapter 34. In some embodiments, the needle assembly 30 may include a needle hub 40 and an introducer needle 42. In some embodiments, the needle hub 40 may be coupled to a proximal end of the catheter adapter 34, and a proximal end of the introducer needle 42 may be secured within the needle hub 40.

In some embodiments, the housing 32 may be secured within a lumen 100 of the catheter adapter 34. In some embodiments, the housing 32 may include a proximal end 44 and a distal end 46. In some embodiments, the proximal end 44 and the distal end 46 may be configured to receive a sharp distal tip 56 of the introducer needle 42 therethrough during manufacture of the catheter system 26. In some embodiments, the sharp distal tip 56 may puncture the proximal end 44 and/or the distal end 46 as the introducer needle 42 is moved distally through the catheter assembly 28 during manufacture. In some embodiments, the housing 32 may include a cavity 78 to contain or encapsulate a portion of a longitudinal shaft 60 of the introducer needle.

In some embodiments, the housing 32 may also include a safety clip 52 located within the cavity. In some embodiments, the safety clip 52 may include an elongated arm portion 64, which may be disposed along a longitudinal axis 94 of the introducer needle 42. In some embodiments, the safety clip 52 may include a barrier feature 54, which may extend from and be angled with respect to the elongated arm portion 64. In some embodiments, the barrier feature 54 may extend in a generally transverse direction from a distal end of the of the elongated arm portion 64. In some embodiments, the barrier feature 54 may extend from the arm portion 64 towards and/or to the introducer needle 42. In some embodiments, the longitudinal shaft 60 may bias the barrier feature 54 and the safety clip 52 outwardly or away from the longitudinal axis 94. In some embodiments, in response to the sharp distal tip 56 of the introducer needle 42 being retracted proximally beyond a position of the barrier feature 54, the barrier feature 54 may move toward and/or beyond the longitudinal axis 94 to shield the introducer needle 42 and prevent the introducer needle 42 from exiting the distal end 46 of the housing 32.

In some embodiments, a first end of the barrier feature 54 may be coupled to the arm portion 64. In some embodiments, a second end of the barrier feature 54 may be coupled to an end portion 65 of the safety clip 52. In some embodiments, the end portion 65 may be generally parallel to the longitudinal axis 94 an/or secured within a groove 67 in response to the sharp distal tip 56 of the introducer needle 42 being retracted proximally beyond a position of the barrier feature 54 and the end portion 65.

In some embodiments, the housing 32 may include a flexible or resilient material such as silicone or another suitable material. In some embodiments, the flexible or resilient material may be impermeable to liquid and/or air. In some embodiments, the housing 32 may be monolithically formed as a single unit or may include more than one parts bonded or coupled together. In either case, the housing 32 may be insulated and/or hermetically sealed to prevent exposure of residual blood to air. In some embodiments, the housing 32 may isolate a distal end of the introducer needle 42 contained therein such that any residual blood on or in that portion of the introducer needle 42 may be isolated from the atmosphere as well as from the external environment. In some embodiments, during manufacture, the sharp distal tip 56 of the introducer needle 42 may puncture or penetrate the proximal end 44 and/or distal end 46 of the housing 32 to enable the longitudinal shaft 60 of the introducer needle 42 to extend through the cavity 78 inside the housing 32.

In some embodiments, an outside surface of the housing 32 may include one or more retainer features 96 configured to engage one or more securement features 98 of the catheter adapter 34. In some embodiments, the securement features 98 may be disposed within the lumen 100 of the catheter adapter 34 such that engagement of the retainer features 96 to the securement features 98 thus secures the housing 32 to the catheter adapter 34. In some embodiments, the retainer features 96 may include one or more recesses in the housing 32 configured to engage one or more protrusions or other securement features 98 in the lumen 100 of the catheter adapter 34. In some embodiments, during manufacture, the housing 32 may be introduced into a proximal end 44 of the housing 32 and advanced in a distal direction within the lumen 100. In this manner, in some embodiments, the securement features 98 may be disposed within the retainer features 96 such that the retainer features 96 engage the securement features 98 to secure the housing 32 to the catheter adapter 34. In some embodiments, the securement features 98 and/or the retainer features 96 may be constructed of the resilient material or another suitable resilient material.

Figure 3:
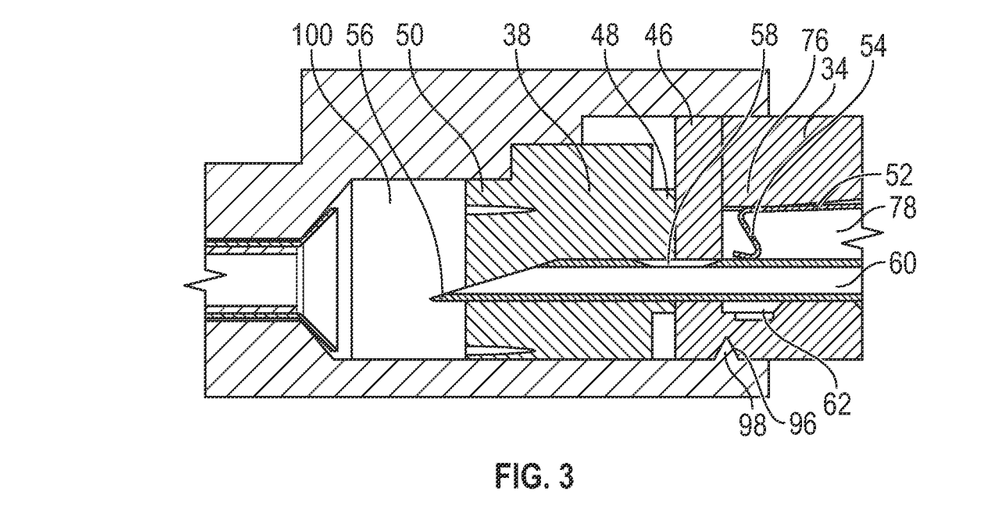
FIG. 3 is an enlarged cross-sectional view of a portion of the catheter system of FIG. 2, illustrating an example tip of the introducer needle extending through an example septum, according to some embodiments.

Referring now to FIG. 3, in some embodiments, the distal end 46 of the housing 32 may be configured to couple to a proximal end 48 of a septum 38 disposed within the lumen 100. In this manner, the housing 32 and the septum 38 may function in combination with each other to prevent environmental contamination from exposure of residual blood to the atmosphere. For example, in some embodiments, the introducer needle 42 may be proximally retracted such that a notch 58 of the introducer needle 42 and the sharp distal tip 56 may be withdrawn into the septum 38. In some embodiments, however, the septum 38 may include a length less than a length or distance between the notch 58 and the sharp distal tip 56, which may be desirable to reduce the size of the catheter adapter 34. In some embodiments, the length less than the length or distance between the notch 58 and the sharp distal tip 56 may also improve securement of the catheter 36 as well as patient comfort while the catheter 33 is dwelling within vasculature. In some embodiments, the length less than the length or distance between the notch 58 and the sharp distal tip 56 may reduce drag force of the introducer needle 42 within the catheter adapter 34.

Nevertheless, in some cases, the septum 38 that includes the length less than the length or distance between the notch 58 and the sharp distal tip 56s smaller may preclude concurrent isolation of both the notch 58 and the sharp distal tip 56 of the introducer needle 42 within the septum 38 as the introducer needle 42 is withdrawn proximally. In some embodiments, as illustrated in FIG. 3, the housing 32 may function in combination with the septum 38 to avoid this problem. For example, the septum 38 in combination with the housing 32 may enable the introducer needle 42 to be retracted within the catheter adapter 34 while maintaining concurrent isolation of both the notch 58 and the sharp distal tip 56, thus avoiding environmental contamination. Specifically, in some embodiments, the notch 58 may be retracted into the housing 32 concurrently with the sharp distal tip 56 being retracted into the septum 38.

In some embodiments, the sharp distal tip 56 of the introducer needle 42 may be retracted proximally into the cavity 78 of the housing 32. In some embodiments, the cavity 78 may include a safety mechanism to maintain the sharp distal tip 56 of the introducer needle 42 within the housing 32 to protect against accidental needle sticks and environmental contamination from residual blood. In some embodiments, the safety mechanism may include the safety clip 52 disposed within the cavity 78 to keep the sharp distal tip 56 protected and to limit movement of the introducer needle 42. In some embodiments, the safety clip 52 and/or barrier feature 54 may be sealed within the cavity 78 after installation.

Figure 4:
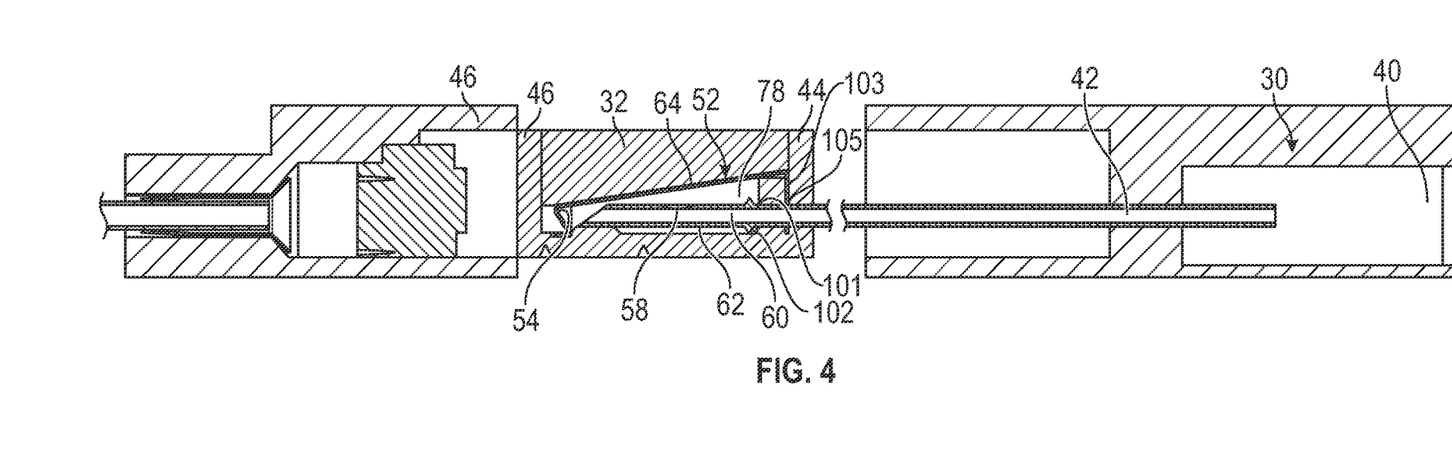
FIG. 4 is a cross-sectional view of the catheter system of FIG. 2, illustrating the introducer needle in a retracted position, according to some embodiments.

Referring now to FIG. 4, in some embodiments, the safety clip 52 may be monolithically formed as a single unit. In some embodiments, the safety clip 52 may be made of metal, plastic, a composite material, or another suitable material.

In some embodiments, actuation of the safety clip 52 by withdrawing the introducer needle 42 proximal to the barrier feature 54 and/or the end portion 65, may occlude the distal end 46 of the housing 32 such that the sharp distal tip 56 of the introducer needle 42 may be precluded from being re-introduced therethrough.

In some embodiments, in response to retraction of the introducer needle 42 in a proximal direction after the safety clip 52 has been actuated, the introducer needle 42 and housing 32 may be removed from the catheter adapter 34. In some embodiments, the introducer needle 42 may include a needle feature 102, such as, for example, a bump, a crimp, or another suitable needle feature on the longitudinal shaft 60 of the introducer needle 42. Retraction of the introducer needle 42 in a proximal direction may cause the needle feature 102 to contact a proximal end 44 of the housing 32 or a proximal wall 103 of the safety clip 52, through which the longitudinal shaft 60 may extend. In some embodiments, the proximal end 44 of the housing 32 may include an opening 101, and an outer diameter of the needle feature 102 may be greater than a diameter of the opening 101, which may prevent the introducer needle 42 from being removed proximally through the opening 101.

In some embodiments, the proximal wall 103 of the safety clip 52 may include an opening 105, and an outer diameter of the needle feature 102 may be greater than a diameter of the opening 105, which may prevent the introducer needle 42 from being removed proximally through the opening 105. In some embodiments, retraction of the introducer needle 42 may cause the needle feature 102 to contact or interfere with the opening 101 or the opening 105. In some embodiments, the contact or the interference may cause the retainer features 96 to disengage from the securement features 98 and/or housing 32 to be pulled from a proximal end of the lumen 100 in response to retraction or withdrawal of the introducer needle 42 in the proximal direction.

In some embodiments, in response to retraction of the introducer needle 42 in the proximal direction, the resilient material that may form the distal end 46 of the housing 32 may deform, thereby releasing the proximal end 48 of the septum 38. In some embodiments, retracting the housing 32 in the proximal direction may pull the distal end 46 of the housing 32 away from the proximal end 48 of the septum 38, thereby removing the housing 32 from the septum 38.

Figure 5A:
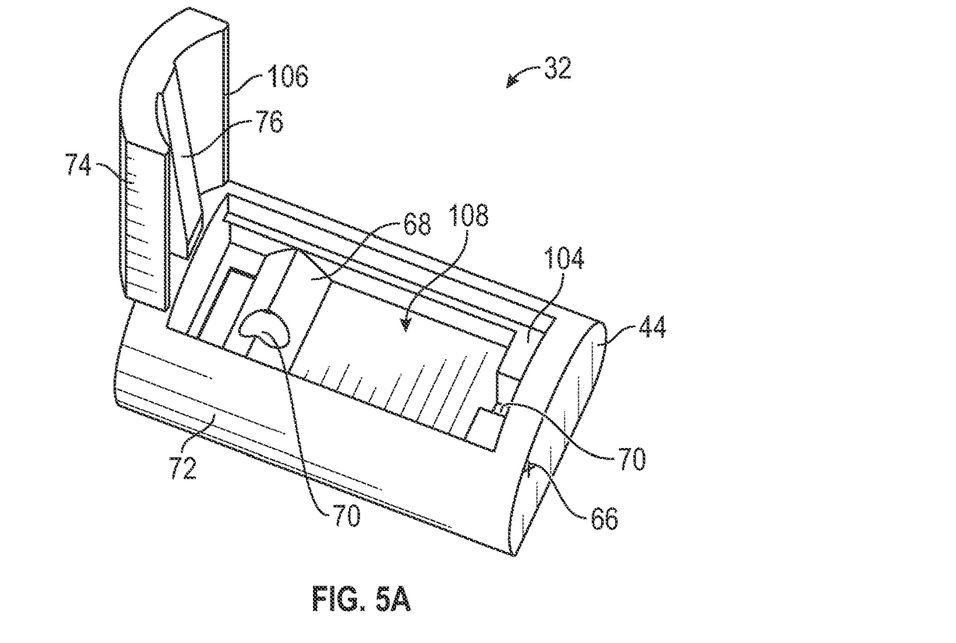
FIG. 5A is an upper perspective view of an example housing, including an upper portion and a lower portion, according to some embodiments.
Figure 5B:
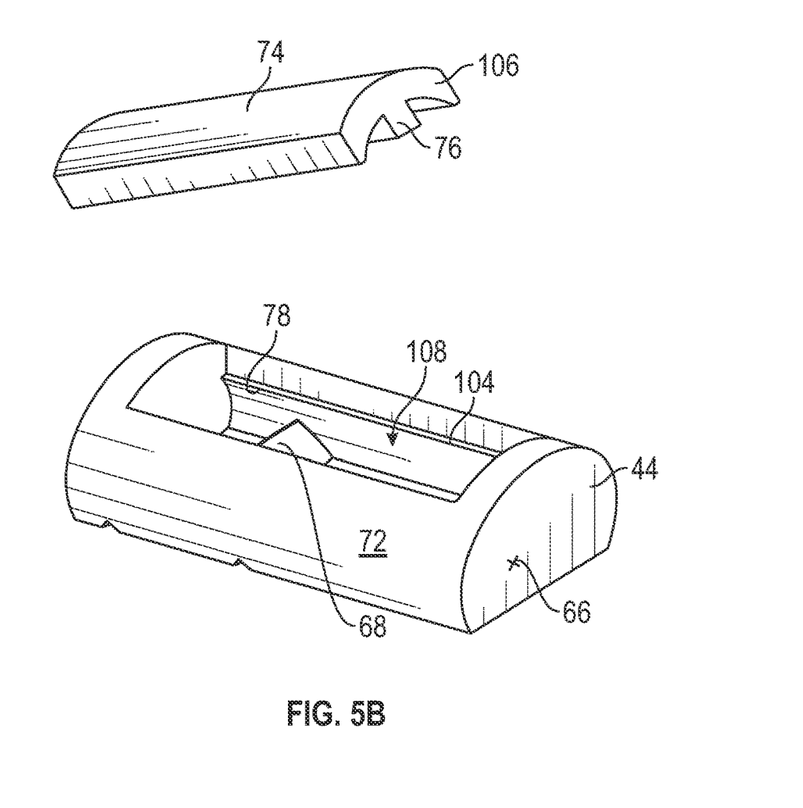
FIG. 5B is a perspective view of the housing of FIG. 5A, including an upper portion and a lower portion, according to some embodiments.
Figure 5C:
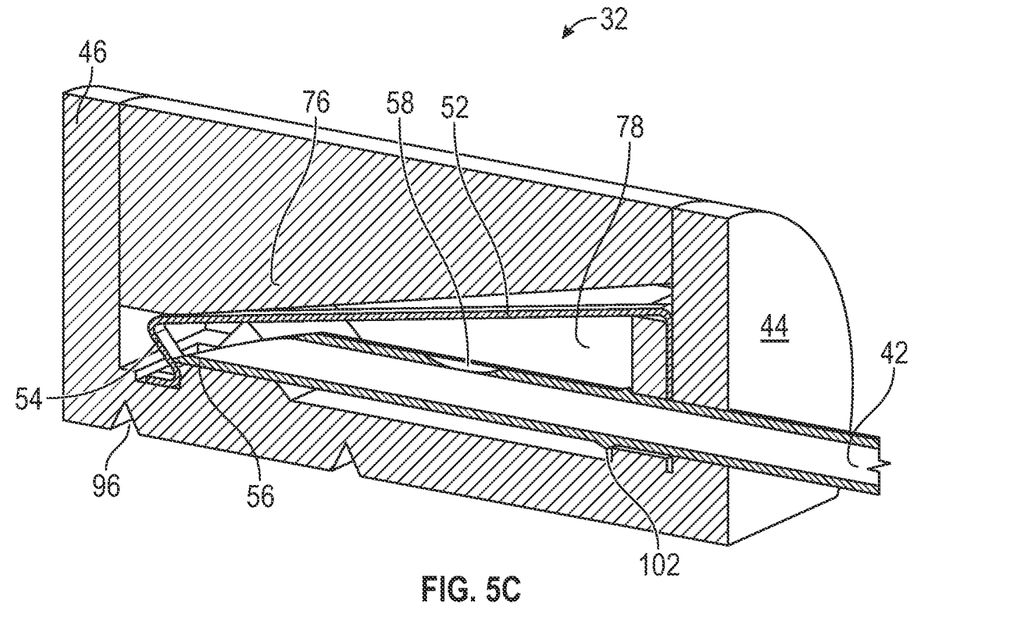
FIG. 5C is a cross-sectional view of the housing of FIG. 5A, illustrating the introducer needle in the retracted position, according to some embodiments.

Referring now to FIGS. 5A-5C, in some embodiments, the housing 32 may include more than one part, which may be coupled together, such as, for example, via bonding. For example, as illustrated in FIGS. 5A and 5B, the housing 32 may include an upper portion 74 and a lower portion 72. In some embodiments, each of the upper and the lower portions 74, 72 may include a shape and dimensions configured such that the upper portion 74 and the lower portion 72 may fit together to form the housing 32. In some embodiments, as illustrated in FIG. 5A, the lower portion 72 may include an opening 108 formed by an edge. In some embodiments, the lower portion 72 may include a ledge 104 or protrusion spaced apart from the edge forming the opening. In some embodiments, the ledge 104 may be L-shaped. In some embodiments, the upper portion 74 may be configured to be received into the opening 108 and supported by the ledge 104 of the lower portion 72. In some embodiments, the upper portion 74 and the lower portion 72 may be coupled together via an interference fit, an adhesive, a mechanical element such as a hinge, or by any other suitable method or device. In some embodiments, the upper portion 74 may be sealed to the lower portion 72 to render the housing 32 airtight.

In some embodiments, the proximal end 44 of the lower portion 72 of the housing 32 may include an access point 66 through which the sharp distal tip 56 of the introducer needle 42 may enter and/or of be withdrawn from the housing 32. In some embodiments, in response to the introducer needle 42 being inserted through the proximal end 44 at the access point 66, the opening 105 may be formed. In some embodiments, the access point 66 may include a visual indicator or mark identifying a desired point of entry for the sharp distal tip 56 of the introducer needle 42. In some embodiments, the access point 66 may include an indentation or other variation in texture, shape, or color of the proximal end 44 of the lower portion 72 through which the sharp distal tip 56 may enter.

In some embodiments, the access point 66 may be situated off-center relative to the proximal end 44 of the housing 32. In these and other embodiments, the introducer needle 42 may extend through the cavity 78 along a line off-of-center relative to the housing 32 to align with the catheter 36. In other embodiments, the access point 66 and the introducer needle 42 may be centered relative to the proximal end 44 of the housing 32.

In some embodiments, the lower portion 72 may include one or more support elements 68, which may include a support channel 70 to support and retain the longitudinal shaft 60 of the introducer needle 42. In some embodiments, the support channel 70 may further direct the sharp distal tip 56 of the introducer needle 42 towards and/or through an exit point in the distal end 46 of the housing 32. In some embodiments, the position of the support channel 70 may be aligned with the catheter 36 such that the support channel 70 may guide the introducer needle 42 into the catheter 36.

In some embodiments, the housing 32 may include a reinforcement rib 76, which may exert a downward force on the safety clip 52. In some embodiments, the upper portion 74 may include the reinforcement rib 76. As illustrated in FIG. 5C, in some embodiments, the reinforcement rib 76 may be inclined. In some embodiments, the reinforcement rib 76 may urge the barrier feature 54 of the safety clip 52 against the longitudinal shaft 60 of the introducer needle 42. In these and other embodiments, the upper portion 74 may be coupled to the lower portion 72 or the upper portion 74 and the lower portion 72 may be monolithically formed as a single unit.

In some embodiments, the cavity 78 may include a length and/or other dimensions sufficient to contain both the sharp distal tip 56 and the notch 58 of the introducer needle 42. In some embodiments, the cavity 78 may include a groove or cutout feature 62 to reduce friction between the cavity 78 and the introducer needle 42 when the introducer needle 42 is introduced through or retracted from the housing 32. In some embodiments, the cutout feature 62 may extend proximally from the support element 68, which may include a protrusion and/or triangle shape.

Figure 6A:
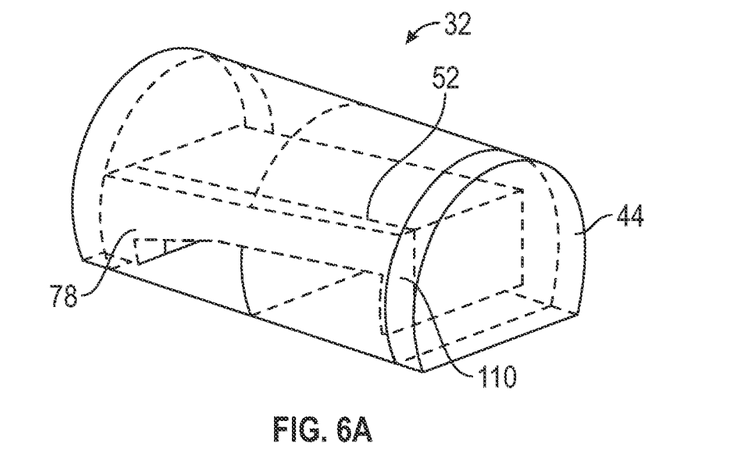
FIG. 6A is a perspective view of another example housing, according to some embodiments.
Figure 6B:
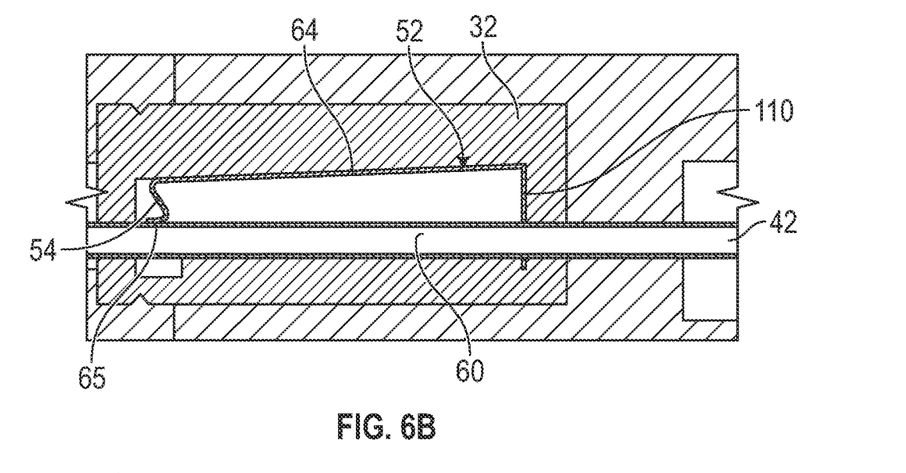
FIG. 6B is a cross-sectional view of the housing of FIG. 6A, illustrating the introducer needle advanced therethrough, according to some embodiments.
Figure 6C:
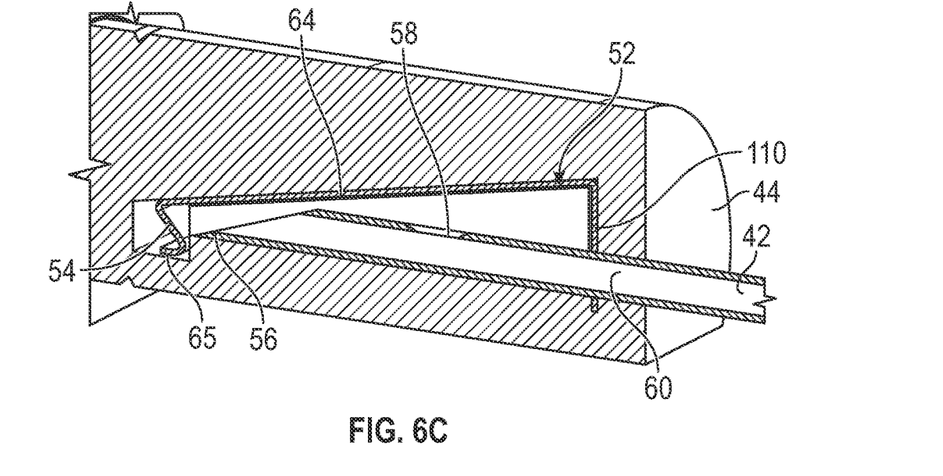
FIG. 6C is a cross-sectional view of the housing of FIG. 6A, illustrating the tip of the introducer needle secured in the housing, according to some embodiments.

Referring now to FIGS. 6A-6C, in some embodiments, the housing 32 may be monolithically formed as a single unit. As illustrated in FIG. 6A, some embodiments may include the housing 32 monolithically formed as a single unit to include the cavity 78. In some embodiments, the safety clip 52 may be secured within the cavity 78. For example, the proximal wall 103 of the safety clip 52 may be coupled to the proximal end 44 of the housing 32 and/or the elongated arm portion 64 may extend in a distal direction from the proximal end 44 of the housing 32. In some embodiments, the elongated arm portion 64 may extend along a top surface of the cavity 78 and/or proximate the reinforcement rib 76. In some embodiments, the barrier feature 54 may extend in a downward direction from a distal end of the elongated arm portion 64.

As illustrated in FIG. 6B, in some embodiments, the reinforcement rib 76 may be compressed in response to the introducer needle 42 extending through the housing 32 and being disposed in the insertion position for insertion into the patient. As illustrated in FIG. 6C, in some embodiments, in response to retraction of the introducer needle 42 in the proximal direction such that the barrier feature 54 moves downward and shields the sharp distal tip 56, the reinforcement rib 76 may expand and put pressure on the elongated arm portion 64, which may facilitate secure shielding of the sharp distal tip 56.

Referring now to FIGS. 7A-7D, in some embodiments, the housing 32 may include a first resilient element 80 and a second resilient element 82 coupled to the first resilient element 80. In some embodiments, the first resilient element 80 may include a coupling element 90, and the second resilient element 82 may include another coupling element 91 coupled to the coupling element 90. In some embodiments, the coupling element 90 and the other coupling element 91 may couple the first and second resilient elements 80, 82 together such that the first and second resilient elements 80, 82 are angled with respect to each other. For example, the first resilient element 80 may be angled at an angle $\alpha$ less than 180° with respect to the second resilient element 82 to form a V-shape 114. In some embodiments, the first and the second resilient elements 80, 82 may include silicone or any other suitable resilient material.

Figure 7A:
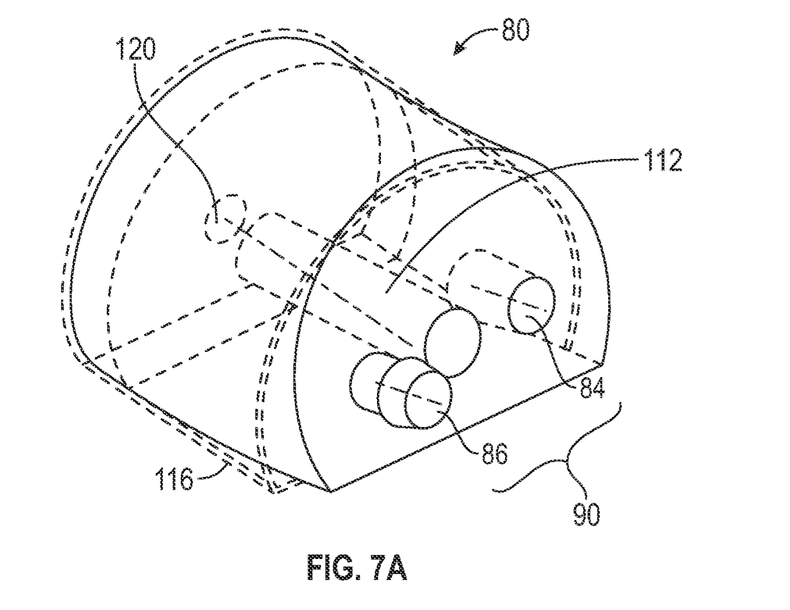
FIG. 7A is a perspective view of an example resilient element, according to some embodiments.
Figure 7B:
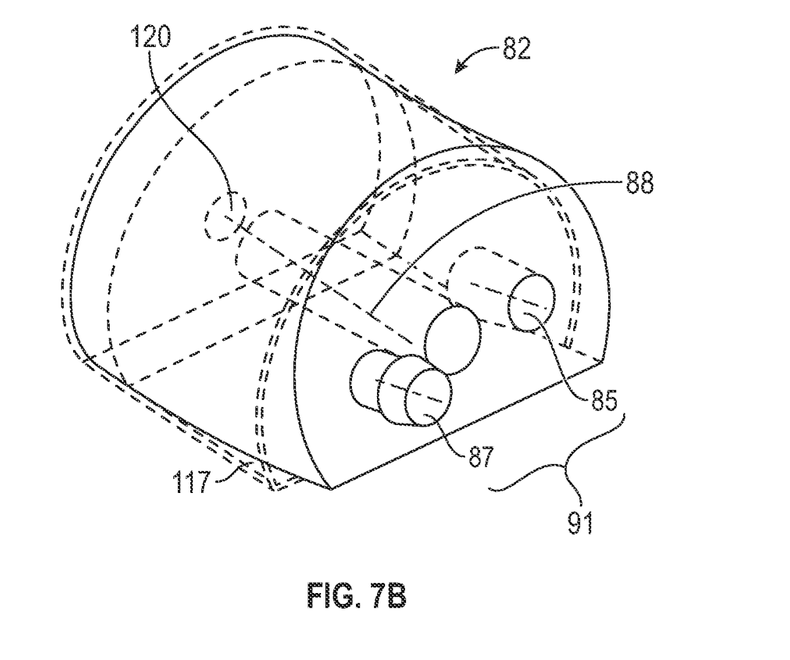
FIG. 7B is a perspective view of another example resilient element, according to some embodiments.

In some embodiments, the coupling element 90 may include, for example, an aperture 84 and a protrusion 86. In some embodiments, the other coupling element 91 may include another aperture 85 configured to receive the protrusion 86 and another protrusion 87 configured to be inserted into the aperture 84.

In some embodiments, the first and second resilient elements 80, 82 may each include a proximal end and a distal end. In some embodiments, the first resilient element 80 may include a first central bore 88 and the second resilient element 82 may include a second central bore 112. In some embodiments, the first central bore 88 and the second central bore 112 align in response to the introducer needle 42 being inserted through the first central bore 88 and the second central bore 112. In some embodiments, the first and second central bores 88, 112 may include similar dimensions such that together they form a central passageway 92 to receive the introducer needle 42.

In some embodiments, at least a portion of one or both of the first and the second central bores 88, 112 may be formed by the introducer needle 42 extending through the first resilient element 80 and/or the second resilient elements 82. In some embodiments, the introducer needle 42 may extend through at least a portion of the first resilient element 80 and/or the second resilient elements 82 to form the central passageway 92.

Figure 7C:
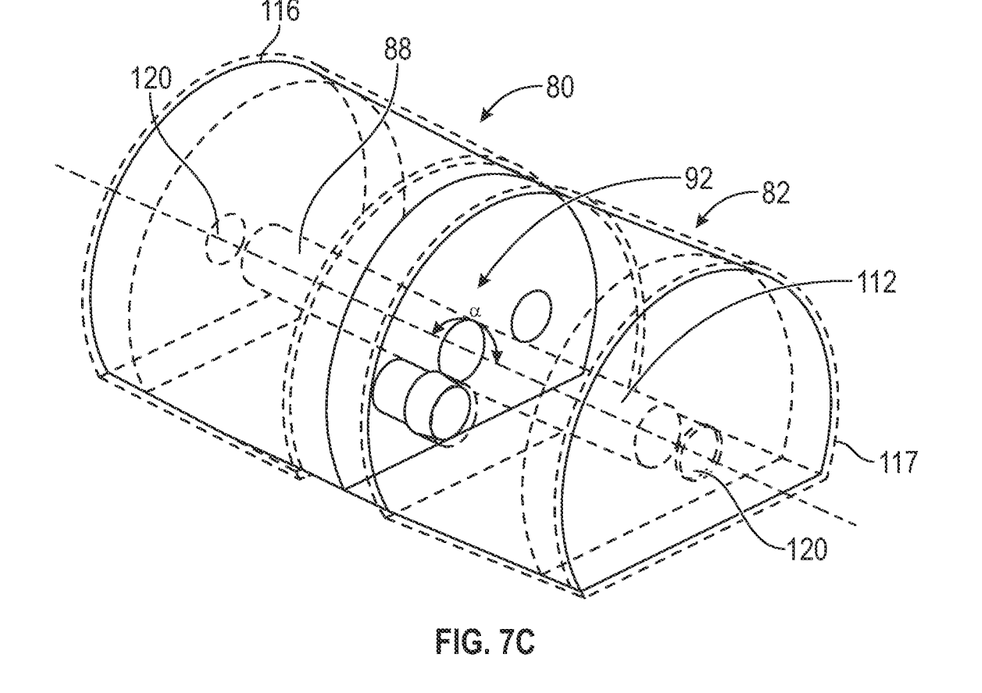
FIG. 7C is a perspective view of an example housing formed from the resilient element of FIG. 7A and the resilient element of FIG. 7B, according to some embodiments.
Figure 7D:
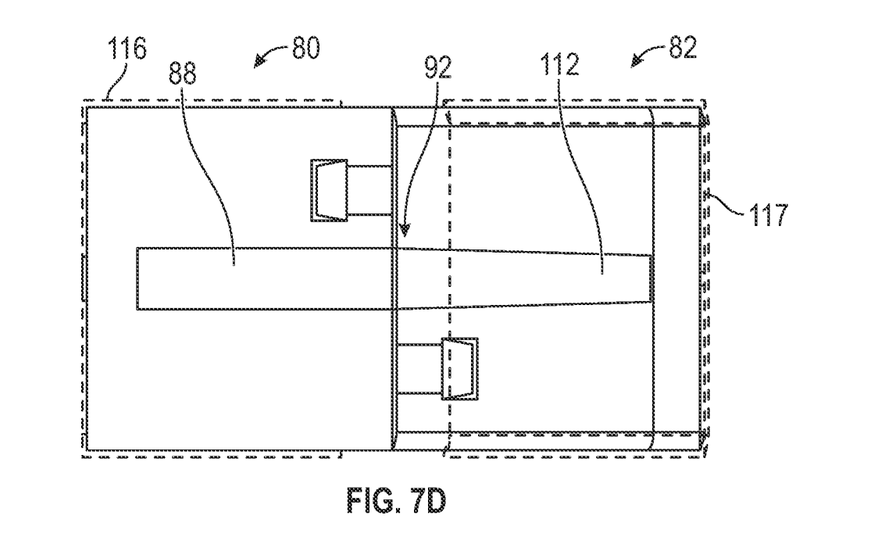
FIG. 7D is a cross-sectional view of the housing of FIG. 7C, according to some embodiments.

In some embodiments, the housing 32 may further include a first exterior covering 116 and/or a second exterior covering 117 to prevent the sharp distal tip 56 of the introducer needle 42 from entering or exiting the housing 32 at a non-designated point. In some embodiments, the first exterior covering 116 and/or the second exterior covering 117 may be rigid. The first exterior covering 116 and/or the second exterior covering 117 may include, for example, aluminum, metal, stainless steel, plastic, or other suitable material. In some embodiments, the first exterior covering 116 may be coupled to at least a portion of an outer surface of the first resilient element 80 and/or the second exterior covering 117 may be coupled to at least a portion of an outer surface of the second resilient elements 82. In some embodiments, the first exterior covering 116 may cover at least a portion of the proximal end of the first resilient element 80 and the second exterior covering 117 may cover at least a portion of the distal end of the second resilient element 82.

In some embodiments, the first exterior covering 116 and/or the second exterior covering 117 may include an aperture 120, which may be configured to receive the introducer needle 42 therethrough.

Figure 8A:
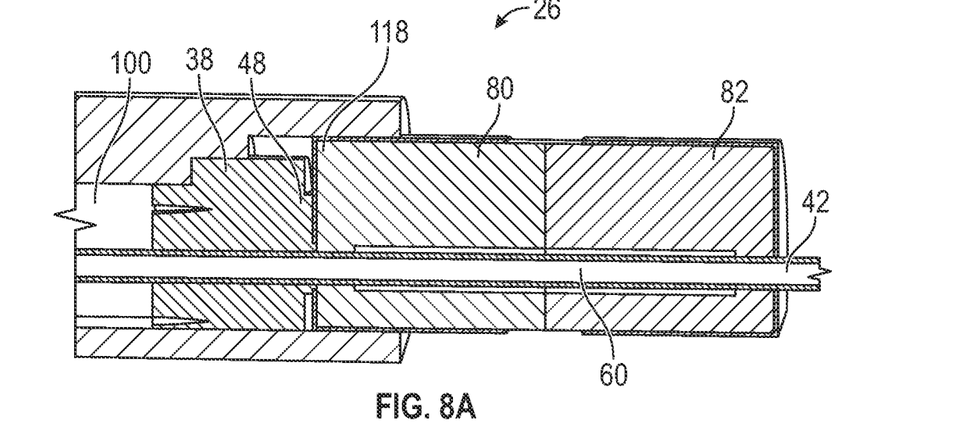
FIG. 8A is a cross-sectional view of an example housing coupled to the septum of the catheter adapter, according to some embodiments.
Figure 8B:
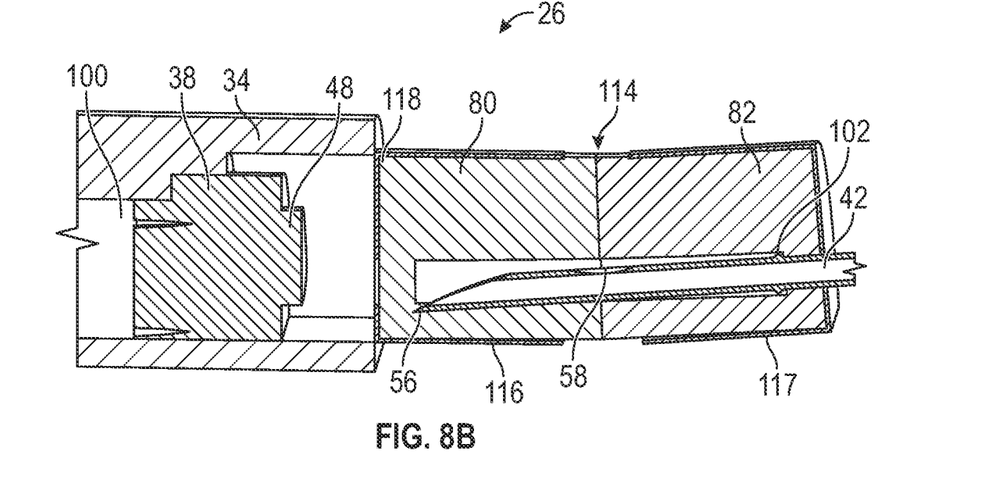
FIG. 8B is a cross-sectional view of the housing and septum of FIG. 8A, illustrating the tip of the introducer needle secured within the housing, according to some embodiments.

Referring now to FIGS. 8A and 8B, in some embodiments, a distal end 118 of the first resilient element 80 may be configured to contact or couple to the septum 38 disposed within the lumen 100 of the catheter adapter 34. This may facilitate the introducer needle 42 extending distally through both the housing 32 and the septum 38 and into the catheter 36. In some embodiments, as illustrated in FIG. 8A, in response to the introducer needle 42 extending through the central passageway 92 into the septum 38, the angle α or a V-shape 114 between the first resilient element 80 and the second resilient element 82 may straighten such that the first resilient element 80 and the second resilient element 82 are aligned with the longitudinal shaft 60 of the introducer needle 42. In some embodiments, as illustrated in FIG. 8B, in response to withdrawing the introducer needle 42 from the septum 38, the V-shape 114 may form.

Formation of the V-shape 114 in this manner may cause the second resilient element 82 to pivot relative to the first resilient element 80 such that the sharp distal tip 56 of the introducer needle 42 is driven into a periphery or wall of the central passageway 92. In some embodiments, the sharp distal tip 56 may thus be secured within the resilient material of the first resilient element 80. In some embodiments, directing the sharp distal tip 56 into the periphery or wall of the central passageway 92 in response to recovery of the V-shape 114 may also prevent further movement of the introducer needle 42. Formation of the V-shape 114 may therefore also secure the notch 58 of the introducer needle 42 within the central passageway 92.

In some embodiments, a proximal wall of the second resilient element 82 or the second exterior covering 117 may include an opening, and an outer diameter of the needle feature 102 may be greater than a diameter of the opening, which may prevent the introducer needle 42 from being removed proximally through the opening 101.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
   a catheter assembly comprising a catheter adapter and a catheter extending distally from the catheter adapter;
   a needle assembly coupled to the catheter assembly, the needle assembly comprising a needle hub and an introducer needle, wherein the needle hub is coupled to a proximal end of the catheter adapter and wherein a proximal end of the introducer needle is secured within the needle hub; and
   a housing retained within a lumen of the catheter adapter, the housing comprising:
      a first resilient element, comprising a proximal end, a distal end, a first central bore, and a coupling element;
      a second resilient element proximal to the first resilient element, wherein the second resilient element comprises a proximal end, a distal end, a second central bore, and another coupling element, wherein the coupling element and the other coupling element are coupled together,
      wherein the first central bore and the second central bore form a central passageway configured to receive a longitudinal shaft of the introducer needle therethrough, wherein the first and second resilient elements are configured to form a V-shape in response proximal retraction of the introducer needle proximal to a distal wall of the first resilient element.

2. The catheter system of claim 1, wherein the housing further comprises a first exterior covering coupled to an outer surface of the first resilient element and a second exterior covering coupled to an outer surface of the second resilient element.

3. The catheter system of claim 2, wherein the first exterior covering and the second exterior covering comprise an aperture to receive the introducer needle therethrough.

4. The catheter system of claim 3, wherein the distal end of the first resilient element is configured to contact or couple to a septum disposed within the lumen.

5. The catheter system of claim 4, wherein in response to the introducer needle extending through the central passageway into the septum, the V-shape straightens along the longitudinal shaft.

6. The catheter system of claim 5, wherein in response to withdrawing the introducer needle from the septum, the first resilient element disengages from the septum to facilitate removal of the housing from the catheter adapter.

7. The catheter system of claim 5, wherein in response to formation of the V-shape, a sharp distal tip of the introducer needle contacts a wall of the central passageway.

8. The catheter system of claim 7, wherein in response to formation of the V-shape, a notch of the introducer needle is secured within the central passageway.

9. The catheter system of claim 1, wherein at least one of the first central bore and the second central bore is formed by the introducer needle.

10. The catheter system of claim 1, wherein the first coupling element comprises a protrusion and an aperture, wherein the second coupling element comprises another protrusion and another aperture.

* * * * *